US006727259B2

(12) United States Patent
Shimada et al.

(10) Patent No.: US 6,727,259 B2
(45) Date of Patent: Apr. 27, 2004

(54) REMEDIAL AGENT FOR NEURAL DEGENERATION

(75) Inventors: Junichi Shimada, Shizuoka (JP); Masako Kurokawa, Mishimi (JP); Ken Ikeda, Shizuoka (JP); Fumio Suzuki, Mishimi (JP); Yoshihisa Kuwana, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/486,823

(22) PCT Filed: Sep. 4, 1998

(86) PCT No.: PCT/JP98/03980

§ 371 (c)(1),
(2), (4) Date: Mar. 3, 2000

(87) PCT Pub. No.: WO99/12546

PCT Pub. Date: Mar. 18, 1999

(65) Prior Publication Data

US 2003/0158214 A1 Aug. 21, 2003

(30) Foreign Application Priority Data

Sep. 5, 1997 (JP) .............................. 9-240565

(51) Int. Cl.⁷ ............................................ A61K 31/522
(52) U.S. Cl. ................................................ 514/263.34
(58) Field of Search ................................ 514/262, 263

(56) References Cited

U.S. PATENT DOCUMENTS

| | | | |
|---|---|---|---|
| 3,641,010 A | 2/1972 | Schweiss et al. | 260/240 D |
| 4,772,607 A | 9/1988 | Badger et al. | 514/263 |
| 5,173,491 A | 12/1992 | Kamoun et al. | 514/265 |
| 5,484,920 A | 1/1996 | Suzuki et al. | 544/268 |
| 5,587,378 A | 12/1996 | Suzuki et al. | 514/264 |
| 5,670,498 A | 9/1997 | Suzuki et al. | 514/212 |

FOREIGN PATENT DOCUMENTS

| | | | |
|---|---|---|---|
| DE | 3843117 | * | 6/1990 |
| DE | 4236331 | | 5/1994 |
| EP | 0590919 | | 4/1990 |
| EP | 0389282 | | 9/1990 |
| EP | 0559893 A1 | | 9/1993 |
| EP | 0565377 | | 10/1993 |
| EP | 0607607 | | 7/1994 |
| EP | 0628311 A1 | | 12/1994 |
| EP | 0698607 | | 2/1996 |
| EP | 0744409 A1 | | 11/1996 |
| JP | 09040652 | * | 2/1997 |

OTHER PUBLICATIONS

Baraldi et al., Current Medicinal Chemistry. 2/3 (707–722) 1995.*
J. Med. Chem., "Structure–Activity Relationships of 8–Styrylxanthines as $A_2$–Selective Adenosine Antagonists", vol. 36, pp. 1333–1342 (1993).
J. Med. Chem., "Effects of Substitution Pattern upon Adenosine Receptor $A_1/A_2$ Affinity", vol. 34, pp. 1431–1435 (1991).
Neuroscience, "Protection Against Kainate–Induced Excitotoxicity by Adenosine $A_{2A}$ Receptor Agonists and Antagonist", vol. 85, pp. 229–237 (1998).
The journal of Neoroscience, "$A_{2A}$ Adenosine Receptor Deficiency Attenuates Brain Injury Induced by Transient Focal Ischemia in Mice", vol. 19(21), pp. 9192–9200 (1999).
Neuroreport, "Blockade of Adenosine $A_{2A}$ Receptors by SCH 58261 Results in Neuroprotective Effects in Cerebral Ischemia in Rats", vol. 9(17), pp. 3955–3959 (1998).
European Journal of Pharmacology, "Adenosine and Cerebral Ischemia: Therapeutic Future or Death of a Brave Concept", vol. 371, pp. 85–102 (1999).
Journal of Neurochemistry, "Protection Against Acute MPTP–Induced Dopamine Depletion in Mice by Adenosine $A_1$ Agonist", vol. 60(2), pp. 768–771 (1993).
Kanda, T. et al: "Adenosine $A_{2A}$ Receptors Modify Motor Function in MPTP–Treated Common Marmosets" Neuropharmacology, NeuroReport 9, 2857–2860 (1998) Aug. 24, 1998, pp. 2875–2860.
Database Medline 'Online! 1996 Mally J et al: "Potential Role of Adenosine Antagonist Therapy in Pathological Tremor Disorders." Database accession No. NLM9364577 XP002205263 *abstract* Pharmacology & Therapeutics England 1996, pp. 243–250.
Heese K. et al: "Nerve Growth Factor (NGF) Expression in Rat Microglia is Induced by Andenosine $A_{2a}$–receptors" Neuroscience Letters, Ireland, Aug. 8, 1997 vol. 231, No. 2, pp. 83–86.

(List continued on next page.)

Primary Examiner—Phyllis G. Spivack
(74) Attorney, Agent, or Firm—Antonelli, Terry, Stout & Kraus, LLP

(57) ABSTRACT

The present invention relates to a therapeutic agent for neurodegenerative disorders, comprising a xanthine derivative represented by formula (I):

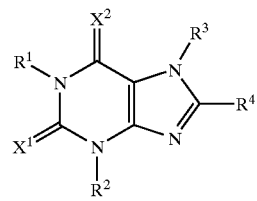

or a pharmaceutically acceptable salt thereof as an active ingredient wherein $X^1$, $X^2$, $R^1$, $R^2$, $R^3$ and $R^4$ are herein defined.

3 Claims, 1 Drawing Sheet

OTHER PUBLICATIONS

Canhao, P. et al: "1,3–Dipropyl–8–cyclopentylxanthine attenuates the NMDA response to hypoxia in the rat hippocampus" Brain Research, 1994, Amsterdam, NL, vol. ½, No. 661, 1994, pp. 265–273.

Lubitz, Von D.K.J.E. et al: "Chronic administration of selective adenosine $A_1$ receptor agonist or antagonist in cerebral ischemia" European Journal of Pharmacology, Amsterdam, NL, vol. 2, No. 256, Apr. 21, 1994, pp. 161–167.

Phillis J.W.: The effects of selective $A_1$ and $A_{2A}$ adenosine receptor antagonists on cerebral ischemic injury in the gerbil Brain Research, Amsterdam, NL, vol. 705, No.½, Dec. 24, 1995, pp. 79–84.

Dalpiza a., et al: "De Novo Analysis of Receptor Binding: Affinity Data of 8–Ethenyl–Xanthine Antagonist to Adenosine $A_1$ and $A_{2A}$ Receptors", Arzneimittel Forschung. Drug Research, Aulendorf, De, vol. 5, No. 47, 1997, pp. 591–594.

Kanda, T et al: "Adenosine A2A Antagonist: A Novel Antiparkinsonian Agent that Does not Provoke Dyskinesia in Parkinsonian Monkeys" Annals of Neurology, Boston, U.S., vol. 4, No. 43, 1998, pp. 507–513.

Saporito, M.S. et al., Neuroscience, 86, 461 (1998).

Glicksman M.A., et al., Neurobiol., 35, 361 (1998).

Olson, L. et al., Neural. Transm. ,(P–D Sect 9), 4 79 (1992).

Vajda, E. J. E., et al, J. Clin. Neurosci., 9, 4 (2002).

Kim, S. An. N.Y. Aca. Sci., 928, 182 (2001).

Jenner, P. et al, Pathol. Biol., 44, 57 (1996).

Emerich, D. F., et al., Expert. Opin. Ther., 1, 467 (2001).

Gray F., et al., Clin Neuropathol., 20, 146 (2001).

Shor–Psner G. et al., J. Aquir. Immune Defic. Sundr., 31, S84 (2002).

* cited by examiner

Table 1
| Compound No. | |
|---|---|
| 1 | 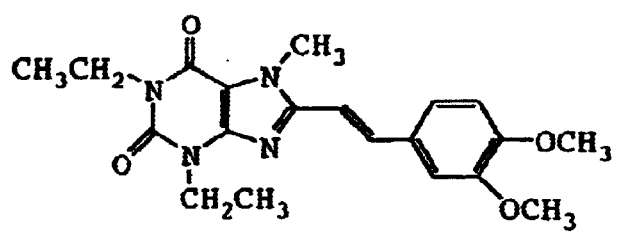 |
| 2 | 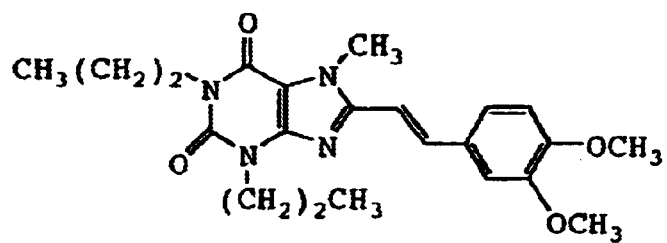 |
| 3 | 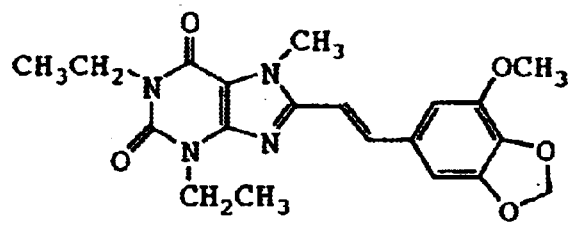 |
| 4 | 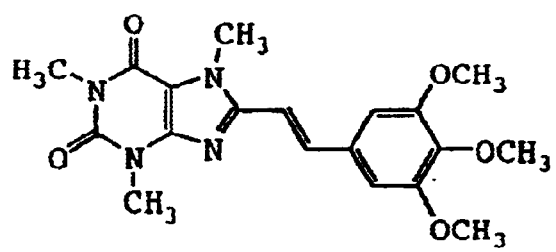 |

REMEDIAL AGENT FOR NEURAL DEGENERATION

FIELD OF THE INVENTION

The present invention relates to a therapeutic agent for neurodegenerative disorders.

BACKGROUND OF THE INVENTION

Most of the compounds according to the present invention are known compounds, and their adenosine $A_2$-receptor antagonism, anti-Parkinson's disease action, anti-depressive action, anti-asthmatic action, inhibitory action on bone absorption and action on central excitation are known [Japanese Published Examined Patent Application No. 26516/72, J. Med. Chem., 34, 1431 (1991), J. Med. Chem., 36, 1333 (1993), WO 92/06976, Japanese Published Unexamined Patent Application No. 211856/94, Japanese Published Unexamined Patent Application No. 239862/94, WO 95/23165, Japanese Published Unexamined Patent Application No. 16559/94 and WO 94/01114).

However, it is not known that said compounds have an inhibitory action on neurodegeneration.

DISCLOSURE OF THE INVENTION

The present invention relates to a therapeutic agent for neurodegenerative disorders, comprising, as an active ingredient, xanthine derivatives represented by formula (I):

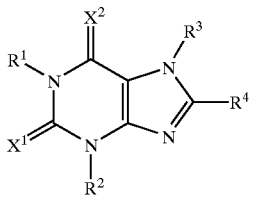

wherein $R^1$, $R^2$ and $R^3$ independently represent hydrogen, lower alkyl, lower alkenyl or lower alkynyl; $R^4$ represents cycloalkyl, $-(CH_2)_n-R^5$ (wherein $R^5$ represents substituted or unsubstituted aryl, or a substituted or unsubstituted heterocyclic group, and n is an integer of 0 to 4), or the following group:

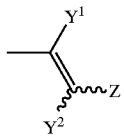

wherein $Y^1$ and $Y^2$ independently represent hydrogen, halogen or lower alkyl, and Z represents substituted or unsubstituted aryl, the following group:

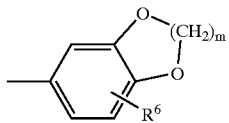

wherein $R^6$ represents hydrogen, hydroxy, lower alkyl, lower alkoxy, halogen, nitro or amino, and m is an integer of 1 to 3, or a substituted or unsubstituted heterocyclic group; and $X^1$ and $X^2$ independently represent O or S, or pharmaceutically acceptable salts thereof.

As the active ingredient for the therapeutic agent for neurodegenerative disorders, preferred compounds are compounds of formula (I) wherein $X^1$ and $X^2$ are O, or pharmaceutically acceptable salts thereof; or compounds of formula (I) wherein $R^4$ is the following-group:

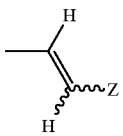

wherein Z has the same meaning as defined above, or pharmaceutically acceptable salts thereof, and specifically preferred compounds are compounds of formula (I) wherein $X^1$ and $X^2$ are O and $R^4$ is the group defined above, or pharmaceutically acceptable salts thereof.

Further, the present invention relates to a method of treating neurodegenerative disorders, which comprises administering an effective dose of a xanthine derivative represented by formula (I) or a pharmaceutically acceptable salt thereof.

Furthermore, the present invention relates to use of a xanthine derivative represented by formula (I) or a pharmaceutically acceptable salt thereof for manufacturing a pharmaceutical composition useful for treatment of neurodegenerative disorders.

Hereinafter, the compound represented by formula (I) is referred to as compound (I).

In the definition of compound (I), the lower alkyl and the lower alkyl moiety in the lower alkoxy mean a straight-chain or branched $C_1$ to $C_6$ alkyl group such as methyl, ethyl, propyl, isopropyl, butyl, isobutyl, sec-butyl, tert-butyl, pentyl, neopentyl and hexyl; the lower alkenyl means a straight-chain or branched $C_2$ to $C_6$ alkenyl group such as vinyl, allyl, methacryl, crotyl, 3-butenyl, 2-pentenyl, 4-pentenyl, 2-hexenyl and 5-hexenyl; the lower alkynyl means a straight-chain or branched $C_2$ to $C_6$ alkynyl group such as ethynyl, propargyl, 2-butynyl, 3-butynyl, 2-pentynyl, 4-pentynyl, 2-hexynyl, 5-hexynyl and 4-methyl-2-pentynyl; the aryl means phenyl or naphthyl; the cycloalkyl means a $C_3$ to $C_8$ cycloalkyl group such as cyclopropyl, cyclobutyl, cyclopentyl, cyclohexyl, cycloheptyl and cyclooctyl; examples of the heterocyclic groups are furyl, thienyl, pyrrolyl, pyranyl, thiopyranyl, pyridyl, thiazolyl, imidazolyl, pyrimidyl, triazinyl, indolyl, quinolyl, purinyl and benzothiazolyl; and the halogen includes fluorine, chlorine, bromine and iodine. The substituted aryl and the substituted heterocyclic group have 1 to 3 independently-selected substituents such as lower alkyl, hydroxy, substituted or unsubstituted lower alkoxy, halogen, nitro, amino, lower alkylamino, di(lower alkyl)amino, trifluoromethyl, tri-fluoromethoxy, benzyloxy, phenyl, phenoxy, lower alkanoyl, lower alkanoyloxy, aroyloxy, aralkanoyloxy, carboxy, lower alkoxycarbonyl, lower alkylcarbamoyl, di(lower alkyl)-carbamoyl, sulfo, lower alkoxysulfonyl, lower alkylsulfamoyl and di(lower alkyl) sulfamoyl. The lower alkyl and the alkyl moiety of the lower alkoxy, lower alkylamino, di(lower alkyl)amino, lower alkanoyl, lower alkanoyloxy, lower alkoxycarbonyl, lower alkylcarbamoyl, di(lower alkyl)-carbamoyl, lower alkoxysulfonyl, lower alkylsulfamoyl and di(lower alkyl) sulfamoyl have the same meaning as the lower alkyl defined above. The halogen has the same meaning as the halogen defined above. Examples of the substituents for the substituted lower alkoxy are hydroxy, lower alkoxy, halogen, amino, azido, carboxy and lower alkoxycarbonyl. The alkyl moiety of the lower alkoxy and lower alkoxycarbonyl has the same meaning as the lower alkyl defined above, and the halogen has the same meaning as the halogen-defined above. The aroyl moiety of the aroyloxy includes benzoyl and naphthoyl. The aralkyl moiety of the aralkanoyloxy includes benzyl and phenethyl.

The pharmaceutically acceptable salts of compound (I) include pharmaceutically acceptable acid addition salts, metal salts, ammonium salts, organic amine addition salts and amino acid addition salts.

The pharmaceutically acceptable acid addition salts of compound (I) include inorganic acid addition salts such as hydrochloride, sulfate and phosphate, and organic acid addition salts such as acetate, maleate, fumarate, tartrate, citrate and methanesulfonate; the pharmaceutically acceptable metal salts include alkali metal salts such as sodium salt and potassium salt, alkaline earth metal salts such as magnesium salt and calcium salt, aluminum salt, and zinc salt; the pharmaceutically acceptable ammonium salts include ammonium and tetramethylammonium; the pharmaceutically acceptable organic amine addition salts include salts with morpholine and piperidine; and the pharmaceutically acceptable amino acid addition salts include salts with lysine, glycine and phenylalanine.

Compound (I) including a novel compound can be produced by the methods disclosed in the above-mentioned publications or according to the methods. The desired compound in the process can be isolated and purified by purification methods conventionally used in synthetic organic chemistry, such as filtration, extraction, washing, drying, concentration, recrystallization and various kinds of chromatography.

In the case where a salt of compound (I) is desired and it is produced in the form of a desired salt, it may be subjected to purification as such. In the case where compound (I) is produced in the free form and its salt is desired, it is dissolved or suspended in a suitable solvent, and then an acid or a base may be added thereto to form the salt.

Compound (I) and pharmaceutically acceptable salts thereof may be in the form of adducts with water or various solvents, which can satisfactorily be used as the therapeutic agent of the present invention.

Some of compounds (I) have optical isomers, and all potential stereoisomers and mixtures thereof can satisfactorily be used as the therapeutic agent of the present invention.

Examples of compound (I) are shown in Table 1.

TABLE 1

| Compound No. | |
|---|---|
| 1 | (structure: 1,3-diethyl-7-methyl-8-(3,4-dimethoxystyryl)xanthine) |

TABLE 1-continued

| Compound No. | |
|---|---|
| 2 | (structure: 1,3-dipropyl-7-methyl-8-(3,4-dimethoxystyryl)xanthine) |
| 3 | (structure: 1-ethyl-3-ethyl-7-methyl-8-(3-methoxy-4,5-methylenedioxystyryl)xanthine) |
| 4 | (structure: 1,3,7-trimethyl-8-(3,4,5-trimethoxystyryl)xanthine) |

Compound 1: (E)-1,3-diethyl-8-(3,4-dimethoxystyryl)-7-methylxanthine (Japanese Published Unexamined Patent Application No. 211856/94)
Melting point: 190.4–191.3° C.
 Elemental analysis: $C_{20}H_{24}N_4O_4$
 Calcd. (%): C 62.48, H 6.29, N 14.57
Found (%): C 62.52, H 6.53, N 14.56
IR(KBr) vmax(cm$^{-1}$): 1697, 1655, 1518
NMR(CDCl$_3$, 270 MHz) δ(ppm): 7.74(1H, d, J=15.5 Hz), 7.18(1H, dd, J=8.3, 1.9 Hz), 7.08(1H, d, J=1.9 Hz), 6.89(1H, d, J=8.3 Hz), 6.77(1H, d, J=15.5 Hz), 4.21(2H, q, J=6.9 Hz), 4.09(2H, q, J=6.9 Hz), 4.06(3H, s), 3.96(3H, s), 3.93(3H, s), 1.39(3H, t, J=6.9 Hz), 1.27(3H, t, J=6.9 Hz)

Compound 2: (E)-8-(3,4-dimethoxystyryl)-1,3-dipropyl-7-methylxanthine (WO 92/06976)
Melting point: 164.8–166.2° C. (Recrystallization from 2-propanol/water)
 Elemental analysis: $C_{22}H_{28}N_4O_4$
 Calcd. (%): C 64.06, H 6.84, N 13.58
Found (%): C 64.06, H 6.82, N 13.80
IR(KBr) vmax(cm$^{-1}$): 1692, 1657
NMR(DMSO-d$_6$, 270 MHz) δ(ppm): 7.60(1H, d, J=15.8 Hz), 7.04(1H, d, J=2.0 Hz), 7.28(1H, dd, J=2.0, 8.4 Hz), 7.18(1H, d, J=15.8 Hz), 6.99(1H, d, J=8.4 Hz), 4.02(3H, s), 3.99(2H, t), 3.90–3.80(2H, m), 3.85(3H, s), 3.80(3H, s), 1.85–1.50(4H, m), 1.00–0.85(6H, m)

Compound 3: (E)-1,3-diethyl-8-(3-methoxy-4,5-methylenedioxy styryl)-7-methylxanthine (Japanese Published Unexamined Patent Application No. 211856/94)
Melting point: 201.5–202.3° C.
 Elemental analysis: $C_{20}H_{22}N_4O_5$
 Calcd. (%): C 60.29, H 5.57, N 14.06
Found (%): C 60.18, H 5.72, N 13.98

IR(KBr) vmax(cm$^{-1}$): 1694, 1650, 1543, 1512, 1433
NMR(DMSO-d$_6$, 270 MHz) δ(ppm): 7.58(1H, d, J=15.8 Hz), 7.23(1H, d, J=15.8 Hz), 7.20(1H, d, J=1.0 Hz), 7.09(1H, d, J=1.0 Hz), 6.05(2H, s), 4.09–4.02(2H, m), 4.02(3H, s), 3.94–3.89(2H, m), 3.89(3H, s), 1.25(3H, t, J=7.2 Hz), 1.13(3H, t, J=6.9 Hz)

Compound 4: (E)-8-(3,4,5-trimethoxystyryl)caffeine (Japanese Published Examined Patent Application No. 26516/72)
IR(KBr) vmax(cm$^{-1}$): 1702, 1667, 1508, 1432
NMR(DMSO-d$_6$, 270 MHz) δ(ppm): 7.61(1H, d, J=16.0 Hz), 7.25(1H, d, J=16.0 Hz), 7.09(2H, s), 4.03(3H, s), 3.85(6H, s), 3.71(3H, s), 3.45(3H, s), 3.21(3H, s)
MS(EI) 386(M$^+$)

Hereinafter, the pharmacological activity of compound (I) is shown by the following Test Examples.

Test Example 1: Inhibitory Action on Neurodegeneration

The experiment was conducted according to the method of Sundstrom et al. (Brain. Res. Bulletin, 21, 257–263 (1988)).

In the experiment, 9- to 10-week-old male C57BL/6NCrj mice (supplied by Nippon Charles River) were used. During the period of preliminary breeding, the animals were kept in a laboratory at room temperature (22 to 24° C.) under 50 to 60% humidity and allowed food and water ad libitum.

1-Methyl-4-phenyl-1,2,3,6-tetrahydropyridine hydrochloride (abbreviated hereinafter as MPTP HCl (RBI Co., Ltd.)) was dissolved at a concentration of 4 mg/ml in physiological saline. A test compound was suspended at a concentration of 1 mg/ml in 0.3% dimethyl sulfoxide (DMSO). Each test group consisted of 9 to 10 animals, and a control group was intraperitoneally given physiological saline, and an MPTP HCl administration group and an MPTP HCl+test compound administration group were intraperitoneally given MPTP HCl (40 mg/kg).

After 1 hour, the control group and the MPTP HCl administration group were orally given 0.3% Tween, and the MPTP HCl+test compound administration group was orally given the test compound (10 mg/kg). After 1 week, the animals were decapitated, and the striatum was removed therefrom under cooling on ice. The striatum was stored in a deep freezer (<–80° C.) before a binding experiment.

A [$^3$H]-mazindol binding test was conducted in the following method. A striatum and 300 μl of buffer (120 mM NaCl, 5 mM KCl, 50 mM Tris, pH 7.9) were put into a micro-centrifuge tube and homogenized by portable homogenizer S-203 (manufactured by Iuchi) and centrifuged at 15,000 rpm, 4° C. for 5 minutes (by KUBOTA 1710). The precipitates were suspended in 300 μl of buffer and then centrifuged again at 15,000 rpm, 4° C. for 5 minutes. The precipitates were suspended in 500 μl of buffer and then distributed into four test tubes in 100 μl portions. The remaining suspension (100 μl) was used for protein quantification. To determine non-specific binding, nomifensine maleate (RBI Co., Ltd.) (final concentration: 10 μM) as an inhibitor of dopamine uptake was added to two test tubes among the four test tubes. The binding reaction was initiated by adding 25 μl of [$^3$H]-mazindol (final concentration: 10 nM) (Spec. Act. 888 GBq/mmol, a product of NET). The mixture was incubated for 1 hour under cooling on ice, and the striatum homogenate was adsorbed onto a glass filter (Whatman, GF/B) in a cell harvester and washed three times with 5 ml of buffer. The radioactivity on the glass filter was measured with a liquid scintillation counter. For each striatum, specific [$^3$H]-mazindol binding was determined by subtracting the average of non-specific [$^3$H]-mazindol binding from the average of total [$^3$H]-mazindol binding.

Protein quantification was conducted by use of a Bio-Rad DC protein assay kit (Bio-Rad Co., Ltd.) with bovine serum albumin (Sigma Co., Ltd.) as a standard. Specific [$^3$H]-mazindol binding was expressed as the amount of bound [$^3$H]-mazindol per unit weight of protein, and the mean±standard error was determined for each group (9–10 animals).

In Table 2, the results are expressed in terms of the amount of specifically bound [$^3$H]-mazindol (fmol/mg protein) in the striatum.

TABLE 2

| Test groups | |
| --- | --- |
| Control | 1140.3 ± 50.0 |
| MPTP HCl | 616.3 ± 32.8### |
| MPTP HCl + compound 1 | 950.9 ± 54.1*** |
| Control | 1219.3 ± 66.4 |
| MPTP HCl | 621.2 ± 27.7### |
| MPTP HCl + compound 2 | 784.8 ± 41.6** |
| MPTP HCl + compound 3 | 794.9 ± 28.5** |
| Control | 1214.8 ± 46.2 |
| MPTP HCl | 674.2 ± 38.1### |
| MPTP HCl + compound 4 | 923.5 ± 51.1** |

**p < 0.01 (compared with the group given MPTP HCl alone).
***p < 0.001 (compared with the group given MPTP HCl alone).
p < 0.001 (compared with the control group).
(n = 9 to 10; Wilcoxon rank sum test)

According to the test results, the reduction of the amount of specifically bound [$^3$H]-mazindol by administration of MPTP HCl was inhibited by compound 1. That is, it was revealed that compound 1 exhibits inhibitory action on degeneration of dopaminergic neurons.

Test Example 2: Acute Toxicity Test

Test compounds were orally or intraperitoneally administered to groups of dd+strain male mice weighing 20±1 g, each group consisting of three mice. Seven days after the administration, the mortality was observed to determine a minimum lethal dose (MLD) of each compound.

The MLD value of Compound 1 was greater than 1000 mg/kg for oral administration.

Compound (I) or pharmaceutically acceptable salts thereof have inhibitory action on neurodegeneration and are useful as a therapeutic agent for neurodegenerative disorders such as Alzheimer's disease, progressive supranuclear palsy, AIDS brain fever, propagating spongy brain fever, Huntington's chorea, multiple sclerosis, amyotrophic lateral sclerosis (ALS), multi-system atrophy, brain ischemia, and attention deficit hyperactivity disorder.

Compound (I) or pharmaceutically acceptable salts thereof can be used as such or in the form of various pharmaceutical compositions. The pharmaceutical compositions of the present invention can be prepared by uniformly mixing an effective amount of compound (I) or a pharmaceutically acceptable salt thereof as an active ingredient with pharmaceutically acceptable carriers. The pharmaceutical compositions are preferably in a unit dosage form suitable for rectal administration, oral or parenteral including subcutaneous, intravenous and intramuscular administration administration, etc.

For preparing a pharmaceutical composition for oral administration, any useful pharmaceutically acceptable carriers can be used. For example, liquid preparations for oral administration such as suspension and syrup can be prepared using water; sugars such as sucrose, sorbitol and fructose; glycols such as polyethylene glycol and propylene glycol; oils such as sesame oil, olive oil and soybean oil; preservatives such as a p-hydroxybenzoate; flavors such as strawberry flavor and peppermint, etc. Powder, pills, capsules and tablets can be prepared using excipients such as lactose, glucose, sucrose and mannitol; disintegrating agents such as starch and sodium alginate; lubricants such as magnesium stearate and talc; binders such as polyvinyl alcohol, hydroxypropyl cellulose and gelatin; surfactants such as fatty acid esters; plasticizers such as glycerin, etc. Tablets and capsules are the most useful oral unit dosage because of the readiness of administration. For preparing tablets and capsules, solid pharmaceutical carriers are used.

Injectable preparations can be prepared using carriers such as distilled water, a salt solution, a glucose solution and a mixture of a salt solution and a glucose solution. The preparation can be prepared in the form of solution, suspension or dispersion according to a conventional method by using a suitable auxiliary.

Compound (I) or a pharmaceutically acceptable salt thereof can be administered orally in the pharmaceutical form described above or parenterally as the injection. The effective dose and administration schedule vary depending on the mode of administration, age, weight, and symptoms of a patient, etc. However, generally, compound (I) or a pharmaceutically acceptable salt thereof is administered in a dose of 1 to 900 mg/60 kg/day, preferably in a dose of 1 to 200 mg/60 kg/day.

Certain embodiments of the present invention are described in the following examples.

EXAMPLE

Example 1

Tablets

Tablets having the following composition were prepared in a conventional manner.

Compound 1 (40 g) was mixed with 286.8 g of lactose and 60 g of potato starch, followed by addition of 120 g of a 10% aqueous solution of hydroxypropyl cellulose. The resultant mixture was kneaded, granulated, and then dried by a conventional method. The granules were refined to give granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter.

The prescription is shown in Table 3.

TABLE 3

| Compound 1 | 20 mg |
|---|---|
| Lactose | 143.4 mg |
| Potato Starch | 30 mg |
| Hydroxypropyl Cellulose | 6 mg |
| Magnesium Stearate | 0.6 mg |
| | 200 mg |

Example 2

Capsules

Capsules having the following composition were prepared in a conventional manner.

Compound 1 (200 g) was mixed with 995 g of Avicel and 5 g of magnesium stearate. The mixture was put in hard capsules No. 4 each having a capacity of 120 mg by using a capsule filler (Model LZ-64, Zanashi) to give capsules each containing 20 mg of the active ingredient.

The prescription is shown in Table 4.

TABLE 4

| Compound 1 | 20 mg |
|---|---|
| Avicel | 99.5 mg |
| Magnesium Stearate | 0.5 mg |
| | 120 mg |

Example 3

Injections

Injections having the following composition were prepared in a conventional manner.

Compound 1 (1 g) was dissolved in 100 g of purified soybean oil, followed by addition of 12 g of purified egg yolk lecithin and 25 g of glycerin for injection. The resultant mixture was made up to 1,000 ml with distilled water for injection, thoroughly mixed, and emulsified by a conventional method. The resultant dispersion was subjected to aseptic filtration by using 0.2 $\mu$m disposable membrane filters, and then aseptically put into glass vials in 2 ml portions to give injections containing 2 mg of the active ingredient per vial.

The prescription is shown in Table 5.

TABLE 5

| Compound 1 | 2 mg |
|---|---|
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

Example 4

Anal Suppository

Formulations for rectal administration having the following composition were prepared in a conventional manner.

Witepsol® H15 (678.8 g, manufactured by Dynamit Nobel, Ltd.) and Witepsol® E75 (290.9 g, manufactured by Dynamit Nobel, Ltd.) were melted at 40 to 50° C. In the resulting molten mixture were uniformly mixed and dispersed Compound 1 (2.5 g), potassium dihydrogen phosphate (13.6 g) and disodium hydrogen phosphate (14.2 g). The resulting dispersion was poured into plastic suppository molds, and gradually cooled to give anal suppositories containing 2.5 mg of the active ingredient per formulation.

The prescription is shown in Table 6.

TABLE 6

| Compound 1 | 2.5 mg |
|---|---|
| Witepzol H15 | 678.8 mg |
| Witepzol E75 | 290.9 mg |
| Potassium dihydrogen phosphate | 13.6 mg |
| Disodium hydrogen phosphate | 14.2 mg |
| | 1000 mg |

Industrial Applicability

The present invention provides a therapeutic agent for neurodegenerative disorders, comprising a xanthine derivative or a pharmaceutically acceptable salt thereof as an active ingredient.

What is claimed is:

1. A method of inhibiting neurodegeneration except Parkinson's disease, which comprises administering an effective dose of a xanthine derivative represented by formula (I):

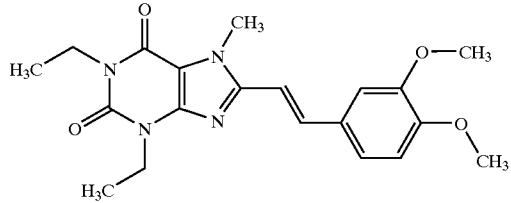

(I)

or a pharmaceutically acceptable salt thereof.

2. A method of treating neurodegenerative disorders except for Parkinson's disease, which comprises administering an effective dose of a xanthine derivative represented by formula (i):

(I)

or a pharmaceutically acceptable salt thereof.

3. A method of treating Alzheimer's disease, which comprises administering an effective dose of the xanthine derivative represented by formula (I):

(I)

or a pharmaceutically acceptable salt thereof.

* * * * *